United States Patent
Yang et al.

(10) Patent No.: US 7,316,651 B2
(45) Date of Patent: Jan. 8, 2008

(54) METHOD FOR AUTOMATICALLY CALIBRATING ELECTRONIC SPHYGMOMANOMETER

(75) Inventors: Paul Yang, Chung Ho (TW); Pin-Hsuan Hung, Chung Ho (TW)

(73) Assignee: Health & Life Co., Ltd., Chung Ho, Taipei (TW)

( * ) Notice: Subject to any disclaimer, the term of this patent is extended or adjusted under 35 U.S.C. 154(b) by 268 days.

(21) Appl. No.: 10/944,791

(22) Filed: Sep. 21, 2004

(65) Prior Publication Data
US 2006/0064023 A1  Mar. 23, 2006

(51) Int. Cl.
*A61B 5/00* (2006.01)
(52) U.S. Cl. ............ 600/490; 600/493; 600/494; 600/496
(58) Field of Classification Search ............ None
See application file for complete search history.

(56) References Cited
U.S. PATENT DOCUMENTS
4,953,557 A * 9/1990 Frankenreiter et al. ..... 600/493

* cited by examiner

*Primary Examiner*—Robert L. Nasser
(74) *Attorney, Agent, or Firm*—Bacon & Thomas, PLLC

(57) ABSTRACT

The present invention discloses a method for automatically calibrating an electronic sphygmomanometer, which pumps air at a predetermined air pressure to a testing electronic sphygmomanometer to simultaneously pressurize a set of pressure sensors set for regular use and at least one other set of pressure sensors being interconnected in the electronic sphygmomanometer to detect whether or not the set of pressure sensors used at regular time is normal. The detected change of pressure during the detection is sent to a control module, and the control module will compare the detected value of each pressure sensor. If the comparison is matched, then it means that the set of pressure sensors used at regular time is normal; if the comparison is mismatched, then the pressure sensors are determined as abnormal and the air valve connected to such pressure sensors is shut, such that when a user uses the electronic sphygmomanometer for the next time, another set of pressure sensors will be started. The present invention can achieve the purpose of allowing users to calibrate the electronic sphygmomanometer on their own without the need of sending the electronic sphygmomanometer to the original manufacturer and further saving time and simplifying the operation.

1 Claim, 6 Drawing Sheets

METHOD FOR AUTOMATICALLY CALIBRATING ELECTRONIC SPHYGMOMANOMETER

BACKGROUND OF THE INVENTION

1. Field of the Invention

The present invention relates to a method for automatically calibrating an electronic sphygmomanometer, more particularly to a method for automatically calibrating an electronic sphygmomanometer by installing an additional set of pressure sensors to the electronic sphygmomanometer, so that users can compare the values of a set of pressure sensors used at regular time and the values of at least one set of pressure sensors through specified air pressure values and settings to determine whether or not the pressure sensors used at regular time are normal; if not, then shut down such pressure sensors, so that users can continue measuring blood pressure for the next time with the normal set of pressure sensors.

2. Description of the Related Art

In general, the pressure sensors (not shown in the figure) of a traditional electronic sphygmomanometer will lose their precision after being used for a period of time, which results in an inaccurate measurement. General users are unable to calibrate the traditional electronic sphygmomanometer on their own, but users have to send the electronic sphygmomanometer back to the original manufacturer for the calibration or the electronic sphygmomanometer is calibrated by an experienced medical professional or a doctor with related equipments. Please refer to FIG. 1 for a prior-art calibration method, which prepares a mercury sphygmomanometer 100 first, and the mercury sphygmomanometer is used as a standard calibrating instrument. With a T-shape interconnected pipe 110, the testing electronic sphygmomanometer 300 is interconnected with the mercury sphygmomanometer 100, while the interconnected pipe 110 is coupled to a manual water pump. Therefore, an air cuff 200 of the calibrating electronic sphygmomanometer 300 is wrapped around the cylinder 400 of a simulated arm of the electronic sphygmomanometer 300. When a power switch (not shown in the figure) situated on the testing electronic sphygmomanometer 300 is pressed, the testing electronic sphygmomanometer 300 is started to switch the operating mode of the testing electronic sphygmomanometer 300 to a testing mode. The air cuff 200 of the testing electronic sphygmomanometer 300 is inflated by the manual air pump 500 and thus the cylinder 400 is pressurized. After the cylinder 400 is pressurized to a specific level, the readings measured by the mercury sphygmomanometer 100 and the testing electronic sphygmomanometer 300 are compared. If the readings match with each other, it is not necessary to calibrate the testing electronic sphygmomanometer 300; if the readings mismatch with each other, it is necessary to adjust the reading of the testing electronic sphygmomanometer 300 to the same value of the reading of the mercury sphygmomanometer 100. The aforementioned procedure is repeated until the reading of the testing electronic sphygmomanometer 300 is equal to the reading of the mercury sphygmomanometer 300. If the adjustment to the same value cannot be made, then it is necessary to replace the pressure sensor or send the electronic sphygmomanometer back to the original manufacturer for calibration. Such arrangement not only wastes time, but also requires professional users to calibrate the electronic sphygmomanometer, which is inconvenient in its use.

SUMMARY OF THE INVENTION

In view of the foregoing shortcomings of the prior art, the inventor of the present invention focused on the problem to conduct extensive researches and experiments and finally invented the method for calibrating electronic sphygmomanometers in accordance with the present invention.

Therefore, it is the primary objective of the present invention to provide a method for calibrating electronic sphygmomanometers, which installs at least one set of pressure sensors to the electronic sphygmomanometer in addition to the set of pressure sensors which is used in regular time and has been already installed in the electronic sphygmomanometer. The set of pressure sensors used at regular time is coupled to an air valve and interconnected with other sets of pressure sensors, so that when the electronic sphygmomanometer is calibrated automatically, the electronic sphygmomanometer controls the control module by entering an external instruction and switches the electronic sphygmomanometer to a testing mode and pressurizes each pressure sensor of the electronic sphygmomanometer by the air pressure set by the air pump, so that the same pressure will be applied to each set of the interconnected pressure sensors in the electronic sphygmomanometer and each value of the pressure sent to the control module can be detected. The control module will use the set of pressure sensors used at regular time to compare with other set of pressure sensors; if the reading of the set of pressure sensors used at regular time matches the reading of each of the other sets of pressure sensors, then the set of pressure sensor used at regular time is normal; if the reading of the set of pressure sensors used at regular time mismatches the reading of each of the other sets of pressure sensors, then the set of pressure sensor used at regular time is abnormal, and the valve connected to the set of pressure sensors used at regular time is turned off, so that users can start using another set of pressure sensors for the use of next time. Such arrangement not only maintains a continuous use of the electronic sphygmomanometer and indicates if it is necessary to send the electronic sphygmomanometer to the original manufacturer, but also allows users to calibrate the electronic sphygmomanometer on their own without sending the electronic sphygmomanometer back to the original manufacturer, and thus achieves the purposes of saving time and simplifying applications.

BRIEF DESCRIPTION OF THE DRAWINGS

The above objects, features and advantages of the present invention will become apparent from the following detailed description taken with the accompanying drawing.

DETAILED DESCRIPTION OF THE PREFERRED EMBODIMENTS

Figure 1:
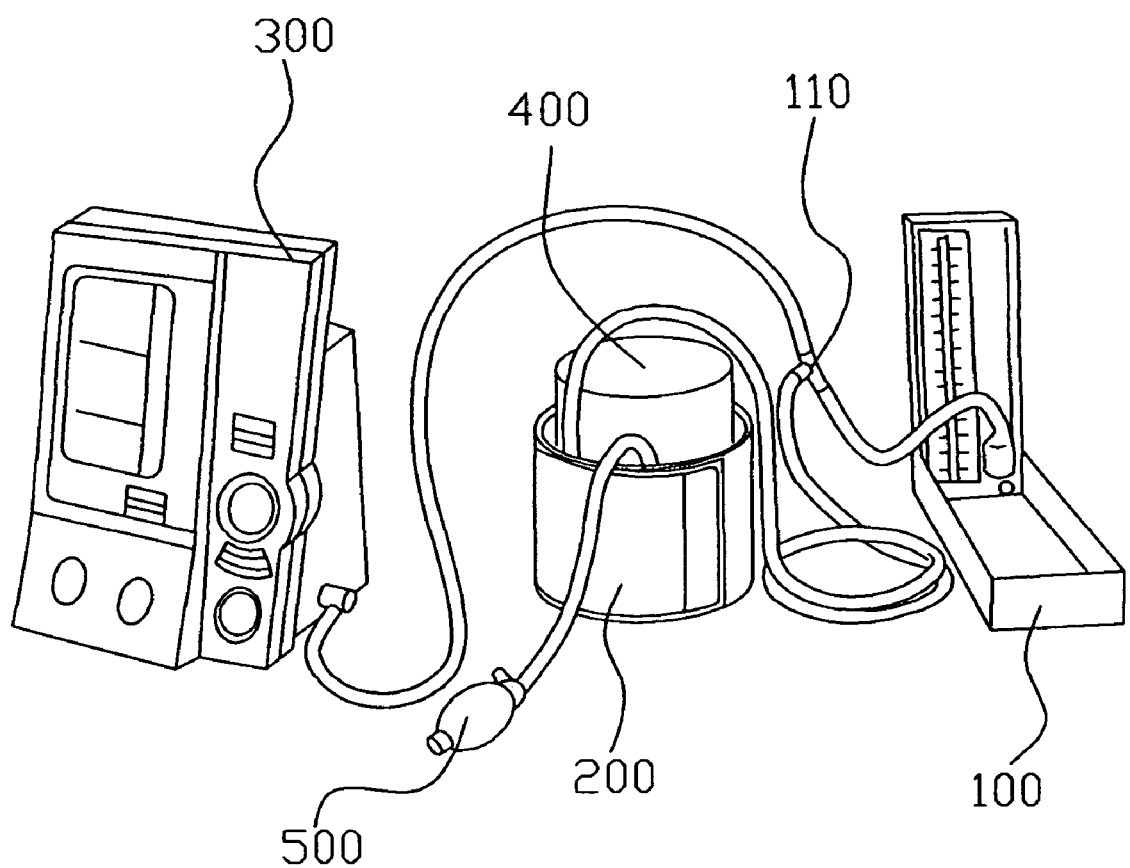
FIG. 1 is an illustrative view of the method of automatically calibrating an electronic sphygmomanometer according to a prior art.
Figure 2:
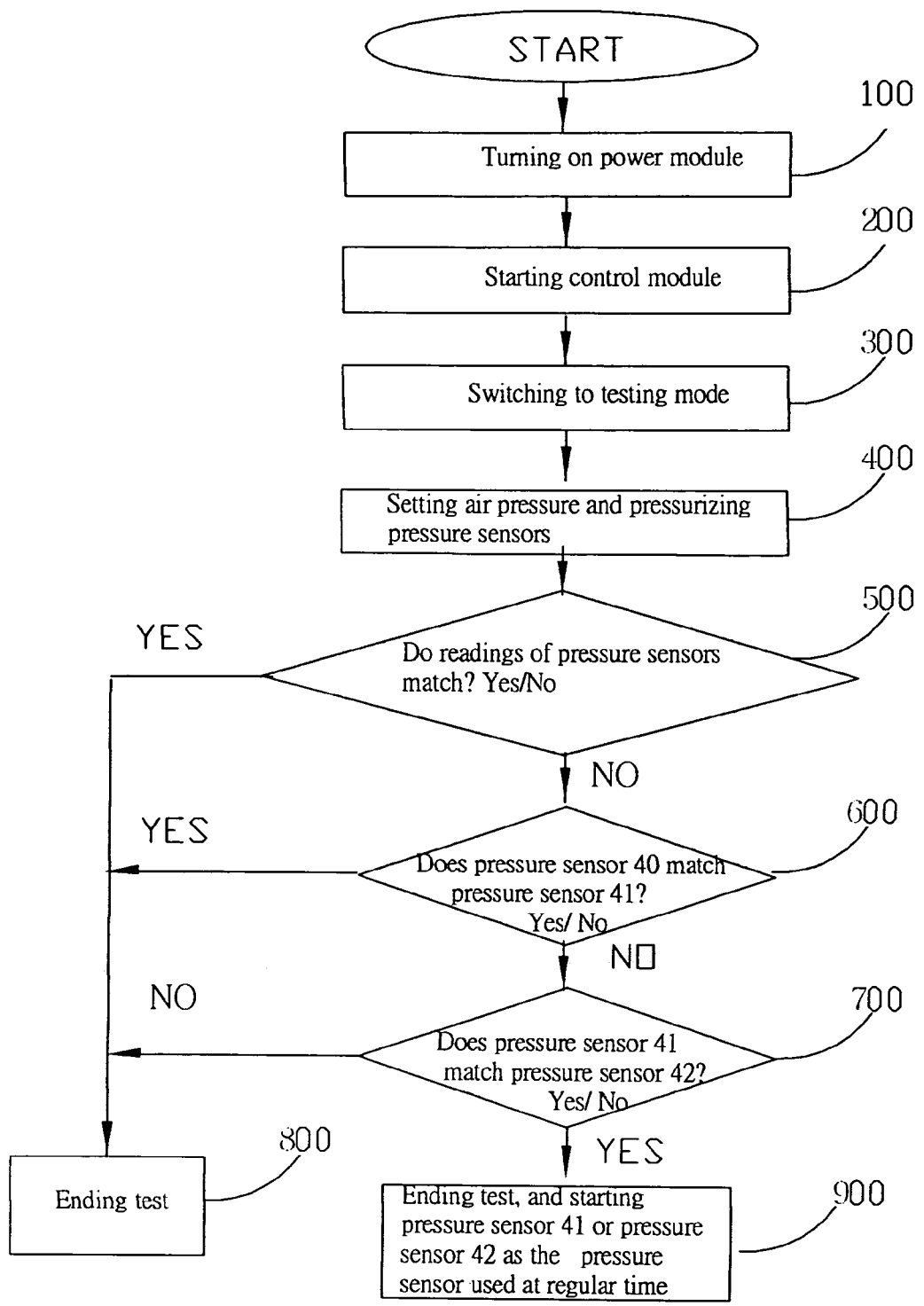
FIG. 2 is a flow chart of the method of automatically calibrating an electronic sphygmomanometer according to the present invention.
Figure 3:
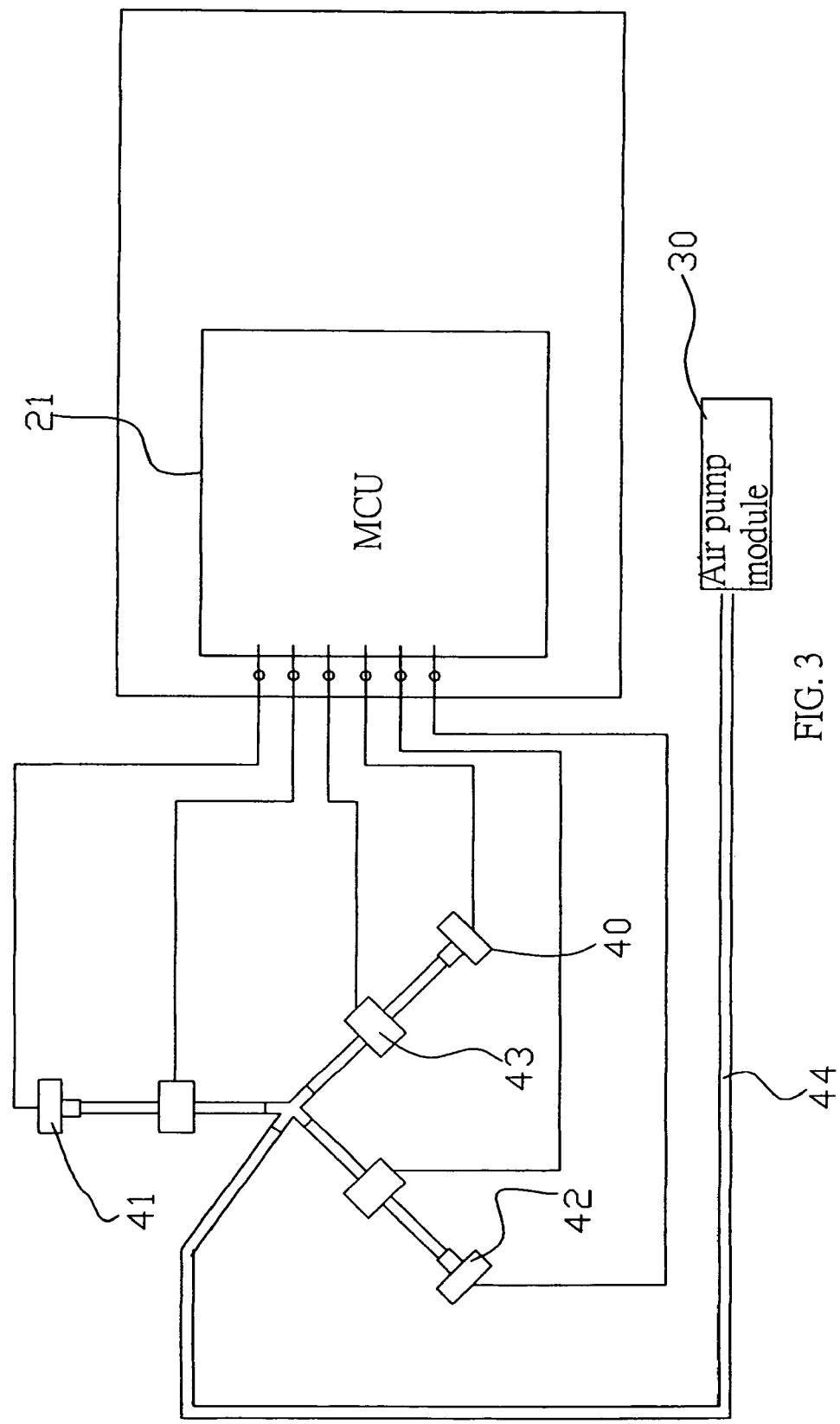
FIG. 3 is an illustrative view of some parts of the electronic sphygmomanometer according to the present invention.
Figure 4:
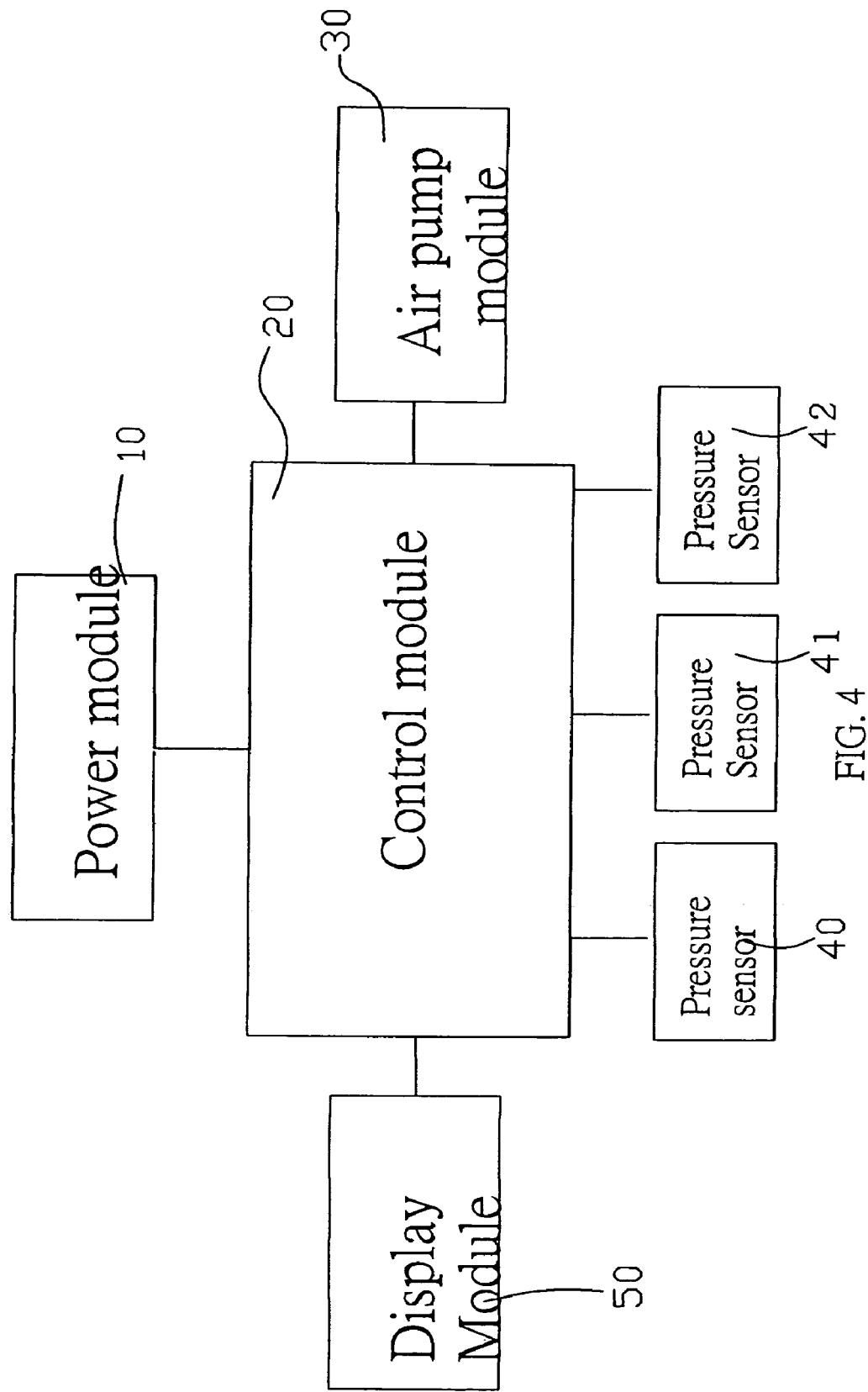
FIG. 4 is a circuit block diagram of the electronic sphygmomanometer according to the present invention.

Please refer to FIGS. 2, 3 and 4 for a method for automatically calibrating an electronic sphygmomanometer according to the present invention, which comprises the steps of:

(Step 100) turning on a power switch of an electronic sphygmomanometer, such that a power module 10 connected to the power switch being turned on (please refer to FIGS. 4 and 5), and the power module 10 supplying the electric power to the control module 20 connected to the power module 10;

(Step 200) setting the control module 20 at the operating mode;

(Step 300) entering a switching instruction for switching the operating mode into a testing mode, so that the control mode 20 switches the mode to the automatic testing mode after receiving the switching instruction;

when the control module 20 is at the testing mode, the air valve of the air pump module 30 is opened first to release the air existing in the air pipe 44 and the air remained in each of the pressure sensors 40, 41, 42, and by then, the pressure sensors 40, 41, 42 are reset to zero and the air valve is shut;

(Step 400) the air pump module 30 pressurizing the electronic sphygmomanometer to the set pressure , and the set pressure value being sent to a display device 50 by the control module 20, and in the meanwhile, the air valve 43 for setting the set of pressure sensor 40 being used at regular time in the electronic sphygmomanometer is opened and the air valve 43 for setting the other set of pressure sensors 40, 41, 42 not used at regular time is opened as well, so that the change of pressure detected from the interconnected pressure sensors 40, 41, 42 are converted into numeric values and sent to a processor 21 of the control module 20, and the processor 21 will send the detected pressure value of each pressure sensor 40, 41, 42 to a display module 50;

(Step 500) comparing the set of pressure sensor 40 used at regular time with other sets of pressure sensors 41, 42;

(Step 800) if the air pressure reading of the pressure sensor 40 set for being used at regular time matches with the air pressure reading of other pressure sensors 41, 42, then the pressure sensor 40 set for being used at regular time is normal, and completing the testing procedure;

(Step 600) if the air pressure reading of the pressure sensor 40 set for being used at regular time mismatches with the air pressure reading of other pressure sensors 41, 42, the pressure sensor 40 set for being used at regular time is abnormal; and shutting the air valve 41 connected to the pressure sensor 40 set for being used at regular time then (step 600) continuously compare the set of pressure sensor 40 used at regular time with one of the other pressure sensor 41 not used at regular time; if the air pressure reading of the pressure sensor 40 set for being used at regular time matches with the air pressure reading of other pressure sensors 41, then (step 800) the pressure sensor 40 set for being used at regular time is normal, and completing the testing procedure;

if the air pressure reading of the pressure sensor 40 set for being used at regular time mismatches with the air pressure reading of other pressure sensors 41, then (step 700) continuously compare the pressure sensor not used at regular time 41 with another pressure sensor 42 not used at regular time; if they are not the same pressure; if they are not the same pressure, then (step 800) the pressure sensor set 40 for being used at regular time is normal and completing the testing procedure;

if they are the same pressure then the pressure sensor 40 set for being used at regular time is abnormal, then (Step 900) starting start another set of pressure sensors 41, 42 when users use the electronic sphygmomanometer for the next time. The present invention can achieve the purpose of allowing users to calibrate the electronic sphygmomanometer on their own without the need of sending the electronic sphygmomanometer to the original manufacturer and further saving time and simplifying the operation.

Figure 5:
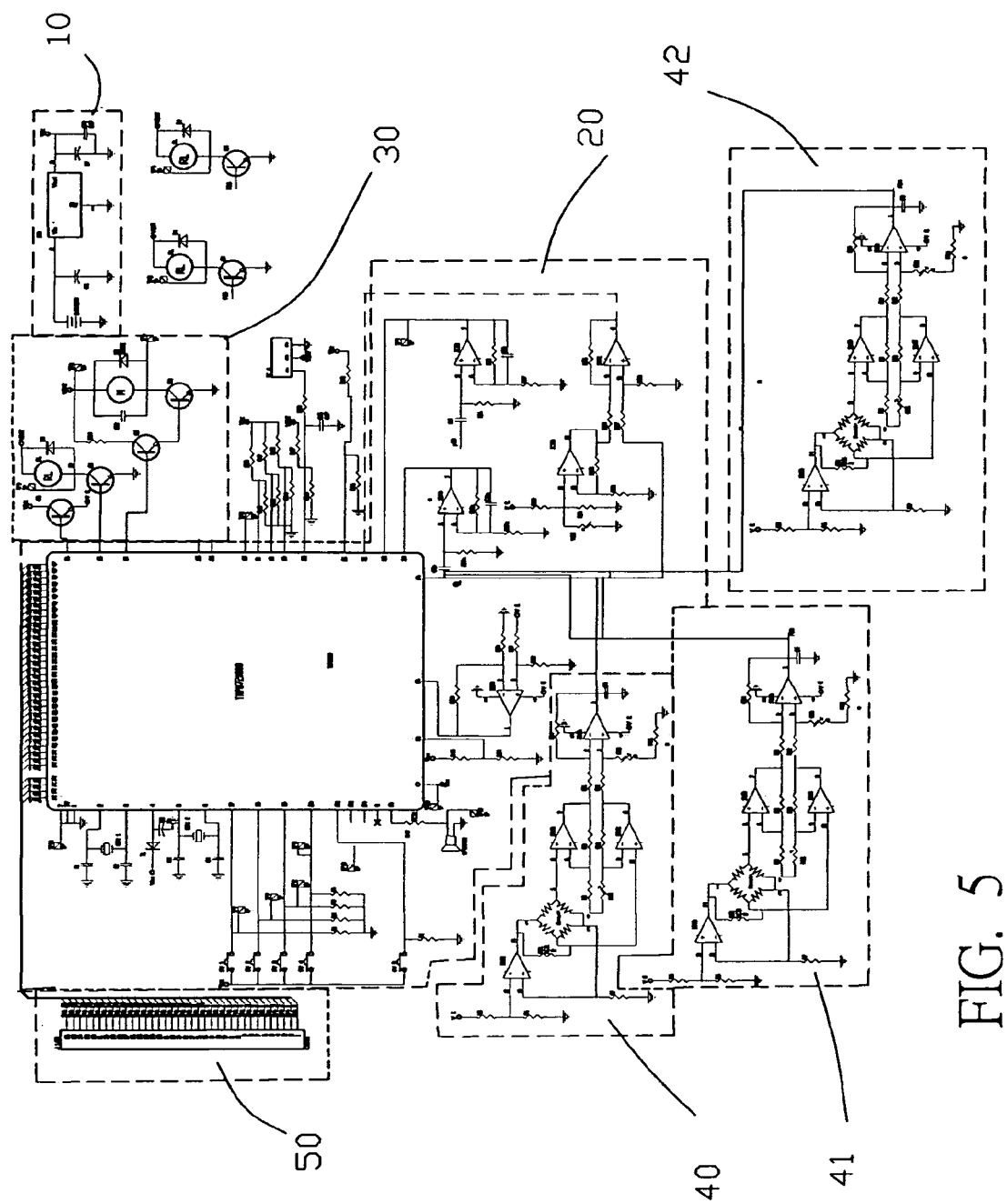
FIG. 5 is a schematic circuit diagram of the electronic sphygmomanometer according to the present invention.
Figure 6:
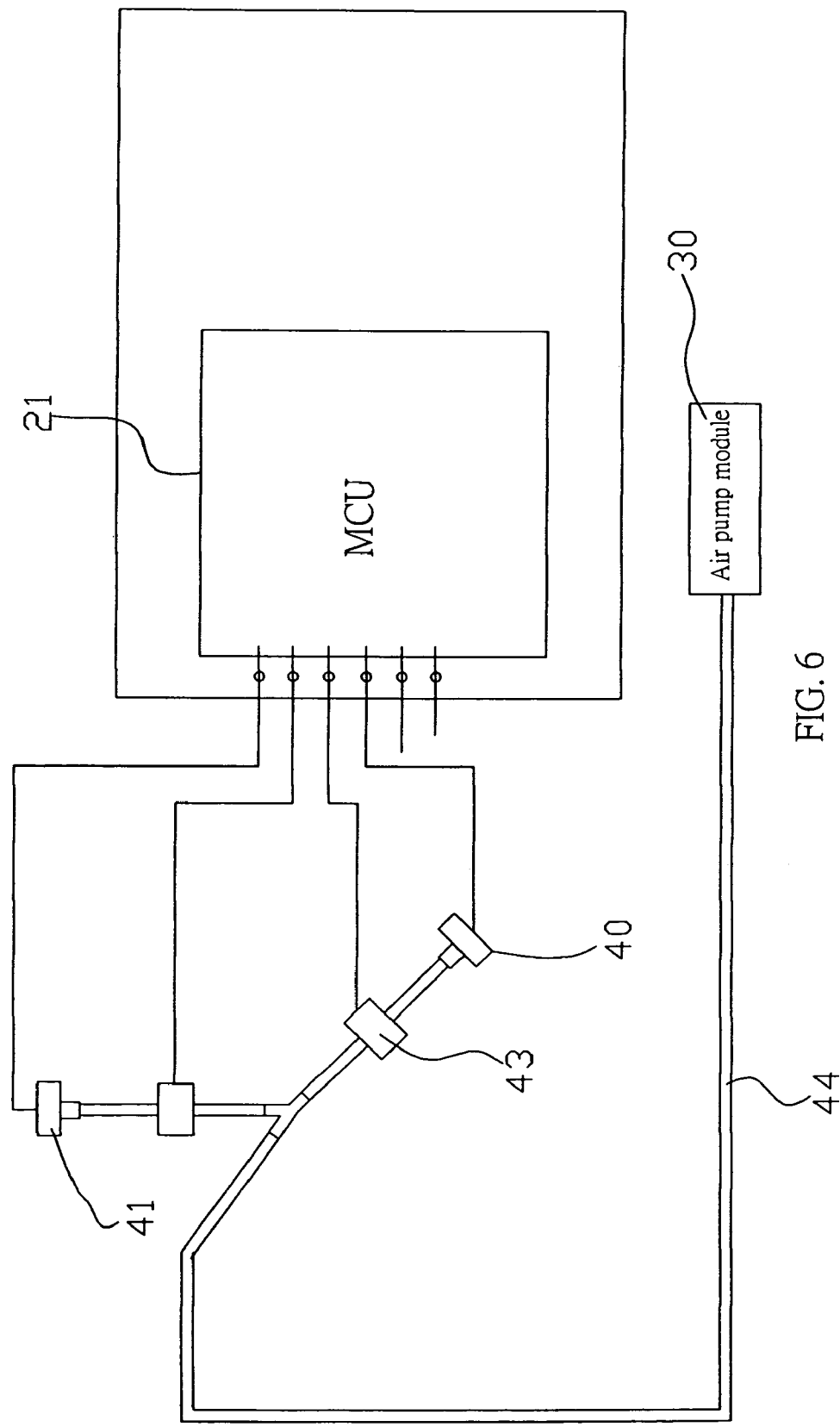
FIG. 6 is an illustrative view of the electronic sphygmomanometer according to another preferred embodiment of the present invention.

Please refer to FIGS. 3, 4, and 5 for the electronic sphygmomanometer corresponding to the calibrating method according to the present invention. The electronic sphygmomanometer comprises a control module 20 and the control module 20 comprises a processor 21, and this embodiment adopts a multitasking processor (MCU) for controlling the actions of the whole electronic sphygmomanometer, and the control module 20 is coupled with a power module 10, an air pump module 30, at least one set of pressure sensors 40 and a display module 50; wherein the air pump module 30 is used for pressurize the pressure sensors 40 and the number of pressure sensors 40 could be two of them (as shown in FIG. 6) or three of them (as shown in FIG. 3), and the pressure sensors 40 are interconnected with each other and interconnected with the air pump module 30. Further, the display module 50 is used for output the related testing values and this embodiment adopts a liquid crystal module as the display module 50.

In summation of the above description, the electronic sphygmomanometer calibrating tool according to present invention herein enhances the performance than the conventional structure and further complies with the patent application requirements and is submitted to the Patent and Trademark Office for review and granting of the commensurate patent rights.

While the invention has been described by way of examples and in terms of preferred embodiments, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method for automatically calibrating electronic sphygmomanometer, said sphygmomanometer including a normally used pressure sensor set and at least second and third additional sensors, comprising the steps of:

turning on a power supply;

setting a control module coupled to a power module at an operating mode;

said control module controlling an air pump module to pressurize an electronic sphygmomanometer to a predetermined pressure value;

opening a valve of a used pressure sensor set in said electronic sphygmomanometer and also opening a valve of another pressure sensor set at the same time, said pressure sensors being capable of detecting a change of pressure, converting said change of pressure into a numeric value, and sending said numeric value to a processor of said control module, said control module sending said predetermined pressure value and a detected pressure value of each pressure sensor of said pressure sensor set to a display module; and said control module comparing the received numeric values, thereby comparing an air pressure value of said used pressure sensor set with an air pressure value of said second pressure sensor; wherein:

if said air pressure reading of the used pressure set matches with said air pressure reading of said second pressure sensor, then said used pressure sensor set is determined to be normal and calibration is ended;

if said air pressure reading of the used pressure sensor set does not match an air pressure reading of said second pressure sensor, then said second pressure sensor is compared with a third pressure sensor;

if an air pressure reading of the second pressure sensor does not match an air pressure reading of the third pressure sensor, then said used pressure sensor is determined to be normal and calibration is ended;

if said air pressure reading of the another pressure sensor matches an air pressure reading of the third pressure sensor, then said used pressure sensor set is determined to be abnormal, and said air value connected to said used pressure sensor set is shut off, in which case, when a blood pressure is measured at a next time, a user is capable of using another normal pressure sensor for the measurement, not only maintaining a continuous use of said electronic sphygmomanometer, but also allowing users to calibrate said electronic sphygmomanometer on their own.

* * * * *